US010822398B2

(12) United States Patent
Taha et al.

(10) Patent No.: US 10,822,398 B2
(45) Date of Patent: Nov. 3, 2020

(54) **POLYCLONAL ANTIBODIES SPECIFIC FOR SEROGROUP X OF *N. MENINGITIDIS* AND USES THEREOF IN DIAGNOSIS**

(71) Applicant: INSTITUT PASTEUR, Paris (FR)

(72) Inventors: Muhamed-Kheir Taha, Saint Maur des Fosses (FR); Alain Agnememel, Freneuse (FR); Francois Traincard, Issy les Moulineaux (FR); Laurence Mulard, Le Kremlin Bicetre (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 15/521,238

(22) PCT Filed: Nov. 17, 2015

(86) PCT No.: PCT/EP2015/076892
§ 371 (c)(1),
(2) Date: Apr. 21, 2017

(87) PCT Pub. No.: WO2016/079157
PCT Pub. Date: May 26, 2016

(65) Prior Publication Data
US 2017/0334975 A1 Nov. 23, 2017

(30) Foreign Application Priority Data

Nov. 18, 2014 (EP) ..................................... 14306832

(51) Int. Cl.
*C07K 16/12* (2006.01)
*G01N 33/569* (2006.01)
(52) U.S. Cl.
CPC .... *C07K 16/1217* (2013.01); *G01N 33/56911* (2013.01); *C07K 2317/33* (2013.01); *G01N 2333/22* (2013.01)
(58) Field of Classification Search
CPC ......... G01N 33/56911; G01N 2333/22; G01N 2333/25; G01N 2400/00; G01N 2400/10; G01N 2469/10; G01N 2800/26; G01N 33/54306; G01N 33/56983; C07K 16/1217; C07K 2317/33; C07K 14/25; C07K 16/1228; C07K 2317/14; C07K 2317/34; C07K 2317/565; A61K 2039/525; A61K 39/00; C12Q 1/025; Y02A 50/476
See application file for complete search history.

(56) References Cited

U.S. PATENT DOCUMENTS

| | | | |
|---|---|---|---|
| 2013/0039927 A1* | 2/2013 | Dewhurst | A61K 39/21 424/159.1 |
| 2016/0166674 A1* | 6/2016 | Pizza | A61K 39/095 424/190.1 |
| 2018/0180610 A1 | 6/2018 | Taha et al. | |

OTHER PUBLICATIONS

Muindi et al. Glycobiology 24: 139-149, Advance Access Publication on Oct. 16, 2013.*
Nato et al. J. Clin. Microbiol. 29: 1447-1452, 1991.*
Allen et al. J. Clin. Microbiol. 15: 324-329, 1982.*
Greenspan et al. Nature Biotechnology 17: 936-937, 1999.*
Boisier P, Nicolas P, Djibo S, Taha MK, Jeanne I, Mainassara HB, Tenebray B, Kairo KK, Giorgini D, Chanteau S. 2007. Meningococcal meningitis: unprecedented incidence of serogroup X-related cases in 2006 in Niger. Clin Infect Dis. 44: 657-663.
Taha MK, Parent Du Chatelet I, Schlumberger M, Sanou I, Djibo S, de Chabalier F, Alonso JM. 2002. Neisseria meningitidis serogroups W135 and A were equally prevalent among meningitis cases occurring at the end of the 2001 epidemics in Burkina Faso and Niger. J Clin Microbiol. 40: 1083-1084.
Terrade A, Collard JM, Nato F, Taha MK. 2013. Laboratory evaluation of a rapid diagnostic test for Neisseria meningitidis serogroup A. Trans R Soc Trop Med Hyg.
Chanteau S, Sidikou F, Djibo S, Moussa A, Mindadou H, Boisier P. 2006. Scaling up of PCR-based surveillance of bacterial meningitis in the African meningitis belt: indisputable benefits of multiplex PCR assay in Niger. Trans R Soc Trop Med Hyg. 100: 677-680.
Chanteau S, Dartevelle S, Mahamane AE, Djibo S, Boisier P, Nato F. 2006. New rapid diagnostic tests for Neisseria meningitidis serogroups A, W135, C, and Y. PLoS Med. 3: e337.
Micoli F, Romano MR, Tontini M, Cappelletti E, Gavini M, Proietti D, Rondini S, Swennen E, Santini L, Filippini S, Balocchi C, Adamo R, Pluschke G, Norheim G, Pollard A, Saul A, Rappuoli R, MacLennan CA, Berti F, Costantino P. 2013. Development of a glycoconjugate vaccine to prevent meningitis in Africa caused by meningococcal serogroup X. Proc Natl Acad Sci U S A. 110: 19077-19082.
Ballard TL, Roe MH, Wheeler RR, Todd JK, Glode MP. 1987. Comparison of three latex agglutination kits and counterimmunoelectrophoresis for the detection of bacterial antigens in a pediatric population. Pediatr Infect Dis J. 6: 630-634.
Nato F, Mazie JC, Fournier JM, Slizewicz B, Sagot N, Guibourdenche M, Postic D, Riou JY. 1991. Production of polyclonal and monoclonal antibodies against group A, B, and C capsular polysaccharides of Neisseria meningitidis and preparation of latex reagents. J Clin Microbiol. 29: 1447-1452.
Xie O, Bolgiano B, Gao F, Lockyer K, Swann C, Jones C, Delrieu I, Njanpop-Lafourcade BM, Tamekloe TA, Pollard AJ, Norheim G. 2012. Characterization of size, structure and purity of serogroup X Neisseria meningitidis polysaccharide, and development of an assay for quantification of human antibodies. Vaccine. 30: 5812-5823.

(Continued)

*Primary Examiner* — Sarvamangala Devi
(74) *Attorney, Agent, or Firm* — Arrigo, Lee, Guttman & Mouta-Bellum LLP

(57) ABSTRACT

Polyclonal antibodies specific for serogroup X of *N. meningitidis* and uses thereof in diagnosis. The present invention is directed to polyclonal antibodies, specific for the capsular polysaccharides of *Neisseria meningitidis* serogroup X (NmX), wherein said antibodies are suitable for in vitro detection of *Neisseria meningitidis* serogroup X in biological fluids without culture. The invention also concerns said polyclonal antibodies in different diagnostic tests and methods, in order to detect Nm X. The invention discloses also a rapid diagnostic test for detecting NmX in a biological fluid, as well as a method for obtaining polyclonal antibodies useful for detecting NmX in biological fluids such as cerebrospinal fluid, serum and urine.

11 Claims, 4 Drawing Sheets

(56) References Cited

OTHER PUBLICATIONS

Figure 1:
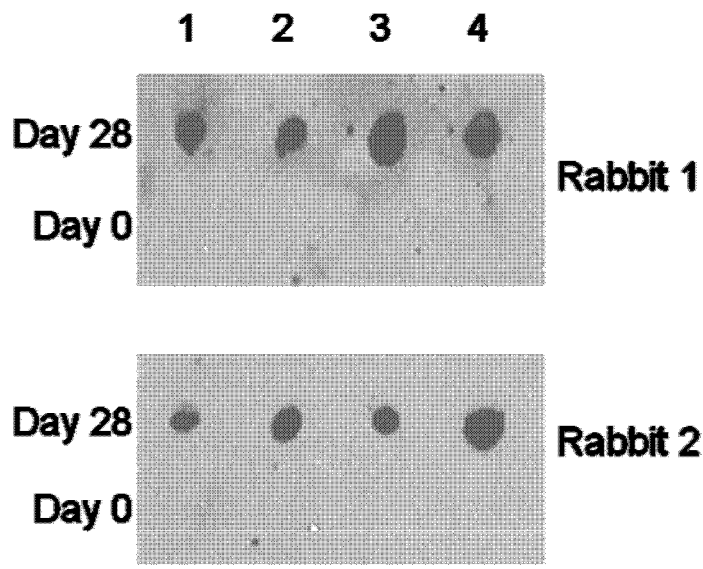

Rissin, DM., et al_ 2010. Single-molecule enzyme-linked immunosorbent assay detects serum proteins at subfemtomolat concentrations. Nat. Biotechnol. 28: 595-600.

Agnememel A. et al. 2015. Development and evaluation of a dipstick diagnostic test for Neisseria meningitidis serogroup X. J Clin Microbiol 53: 449-454.

Fatima Reyes et al. "A novel monoclonal antibody to Neisseria meningitides serogroup X capsular polysaccharide and its potential use in quantitation of meningococcal vaccines", Biologicals, vol. 42, n°6, 2014.

Angela M. C. Rose et al "Meningitis Dipstick Rapid Test : Evaluating Diagnostic Performance during an Urban Neisseria meningitidis Serogroup A Outbreak, Burkina Faso, 2007" PLOS ONE, vol. 5, n°6, 2010.

Alain Agnememel et al : "Characterization and immunogenicity of Neisseria meningitides serogroup X capsular polysaccharide a step forward for rapid diagnostic test", Abstract book EMGM meeting 2013, p. 33.

AFSSAPS Report, 25.11.2009, by Dr Natacha Charler-Bret.

David R. Bundle et al : "Studies on the Group-specific Polysaccharide of Neisseria meningitidis Serogroup X and an Improved Procedure for its Isolation", The Journal of Biological Chemistry, vol. 249, N°15, 1974, 4797-4801.

A. van der Ende et al : "Comparison of Commercial Diagnostic Tests for Identification of Serogroup Antigens of Neisseria meningitides", Journal of Clinical Microbiology, 1995, 3326-3327.

Extended European Search Report in Application No. 14306832.8, dated Apr. 20, 2015.

International Search Report and Written Opinion for PCT/EP2015/076892, dated Feb. 22, 2016.

Ritter M A, "Polyclonal and Monoclonal Antibodies," Methods in Molecular Medicine, vol. 40: Diagnostic and Therapeutic Antibodies, Aug. 1, 2000.

Communication Pursuant to Article 94(3) EPC, European Application No. 15798013.7, dated Oct. 9, 2018.

O'Ryan et al., "A Multi-Component Meningococcal Serogroup B Vaccine (4CMenB): The Clinical Development Program," Drugs, 74:15-30 (2014).

Hong et al., "Could the multicomponent meningococcal serogroup B vaccine (4CMenB) control Neisseria meningitidis capsular group X outbreaks in Africa?," Vaccine, 31:1113-1116 (2013).

Collard et al., "Epidemiological changes in meningococcal meningitis in Niger from 2008 to 2011 and the impact of vaccination," BMC Infect Dis., 13:576 (2013).

European Centre for Disease Prevention and Control. 2013. Annual Epidemiological Report 2012. Reporting on 2010 surveillance data and 2011 epidemic intelligence data. Stockholm: ECDC. Extract p. 168-172 + i) -> xvi).

Chanteau et al., "Development and testing of a rapid diagnostic test for bubonic and pneumonic plague," Lancet., 361:211-216 (2003).

Scaviner et al., "Protein Displays of the Human Immunoglobulin Heavy, Kappa and Lambda Variable and Joining Regions," Exp. Clin. Immunogenet., 16:234-240 (1999).

Kaas et al., "IMGT Colliers de Perles: Standardized Sequence-Structure Representations of the IgSF and MhcSF Superfamily Domains," Current Bioinformatics, 2:21-30 (2007).

Payne et al., "Clinical laboratory applications of monoclonal antibodies" Clinical Microbiology Reviews, 313-329 (1988).

Ala'adeen D A A et al, The meningococcal transferrin-binding proteins 1 and 2 are both surface exposed and generate bactericidal antibodies capable of killing homologous and heterolouous strains, Vaccine, vol. 14, No. 1, 1996, pp. 49-53.

Clezardin P et al, Tandem Purification of IgM Monoclonal Antibodies From Mouse Ascites Fluids by Anion-Excange and Gel Fast Protein Liquid Chromatography, Chrom. 18 261, 1986, pp. 425-433.

\* cited by examiner

POLYCLONAL ANTIBODIES SPECIFIC FOR SEROGROUP X OF *N. MENINGITIDIS* AND USES THEREOF IN DIAGNOSIS

The present invention is in the domain of bacterial detection, specifically detection of *Neisseria meningitidis* (Nm) serogroup X and diagnostic kits allowing the detection of said serogroup, preferably in a biological sample.

*Neisseria meningitidis* (Nm) is an exclusively human capsulated bacterium that can provoke severe invasive infections such as meningitis and septicemia (1). Meningococcal disease is still a major public health concern due to potential epidemic spread. While the disease occurs sporadically in Europe and North America, it is responsible for major recurrent epidemics in Africa, occurring generally in small clusters, with seasonal variation.

The largest incidence of meningococcal disease occurs in an area of sub-Saharan Africa known as the African meningitis belt (2), which stretches from Senegal in the west to Ethiopia in the east. During the dry season, dust winds, cold nights and upper respiratory tract infections combine to damage the nasopharyngeal mucosa, increasing the risk of meningococcal disease. Moreover, transmission of *N. meningitidis* may be facilitated by overcrowded housing and by large population displacements at the regional level due to pilgrimages and traditional markets. This combination of factors explains the large epidemics which occur during the dry season in the meningitis belt.

The bacterial capsular polysaccharide determines the 12 Nm serogroups currently described. Six serogroups (A, B, C, Y, W and X) are responsible for the vast majority of cases of meningococcal disease worldwide. However, they differ in their global frequencies and geographical distribution (3). This distribution impacts on vaccination strategies, which for the most part involve the established polysaccharide-based vaccines against serogroups A, C, Y and W. In addition, an innovative recombinant protein-based vaccine was recently licensed in Europe and Australia against meningococci of serogroup B (4). This multicomponent vaccine targets conserved proteins among meningococci regardless of their serogroup. Therefore, it has the potential to cover non-serogroup B isolates such as those of serogroup X (5). In the meningitis belt, *N. meningitidis* serogroup A (NmA) predominated prior to the introduction of the NmA polysaccharide-protein conjugate vaccine (MenAfriVac™) (6), while other serogroups, mainly serogroups W (NmW) and X (NmX), were also detected and still are. Of particular concern, outbreaks due to isolates of NmW and NmX were recently reported in Africa (7-9). Surveillance of the distribution of meningococcal serogroups is therefore important and its comprehensiveness will benefit from diagnosis tools that can be widely used at the bedside.

Indeed, the WHO strategy for controlling epidemic meningococcal disease, especially in the *meningitidis* belt is based on an early and accurate detection and rapid implementation of mass vaccination using vaccines against the appropriate serogroups. It is thus imperative to rapidly and reliably identify the serogroups involved in meningococcal infection, in order to select the most appropriate vaccine. This appropriate vaccination allows the control of the epidemic clonal spread and thus plays an essential role in limiting the incidence of the outbreaks. An error in the detection of the serogroup impairs and delays the efficacy of this control, emphasizing the importance of the sensitivity and specificity of the serogroup determination.

Two strategies are generally applied for detecting the *N. meningitidis* serogroups involved in a meningococcal infection. The first one is the classic culture with subsequent identification of serogroups using specific antisera. The second one is based on the direct detection of the serogroups in a biological sample from the diagnosed or affected individuals.

With respect to culture isolation, this technique, with strain serogrouping by immune specific antisera, is generally considered as one of the reference standards for identification of *N. meningitidis* serogroups, since this technique is generally considered as specific. It however necessitates a well-equipped laboratory with specialized technicians for the culture, rendering this technique poorly adapted to field detection, especially in Africa, where laboratory facilities can be at some distance away from the area of sample collection, necessitating special transport and preservation conditions of the samples. The time taken for sample transfer as well as the hot, dusty conditions experienced during the *meningitidis* season can lead to high levels of sample contamination. Moreover, the early antibiotherapy recommended in case of a suspected infection diminishes the efficacy of this method. It has also been reported that the specific antisera, used for serogroup identification on strains, do not accurately detect serogroup X and/or give rise to false-positive scores (Afssaps report, 25 Nov. 2009, by Dr Natacha Charler-Bret).

Regarding the non-culture tests, they rely either on immune detection or on genetic detection. Genetic detection is carried out generally by multiplex PCR method. This method is highly specific and very sensitive. It takes however several hours before a result can be obtained. Moreover, this technique is expensive and requires well-equipped laboratories with specialized technicians; this method is thus not well adapted to field conditions.

The non-culture tests based on immune detection of *N. meningitidis* were until recently essentially limited to latex agglutination tests on cerebrospinal fluid (CSF), such as Pastorex (Bio-Rad Laboratories, Inc.). Latex agglutination tests are rapid, sensitive, less labour-intensive and much less expensive than routine culture tests. These tests are however not routinely recommended, because they do not differentiate between serogroups W (previously known as W135) and Y, do not detect serogroup X, and their performance under field conditions lacking basic laboratory equipment is presumably weak. Furthermore, these kits require cold storage and well-trained technicians for the read-out and they may result in a few indeterminates, false negatives, and false-positives.

Recently, an immunochromatography dipstick rapid diagnostic test (RDT) for the identification of *N. meningitidis* serogroups A, C, Y and W (10-11) has been developed and validated. This major achievement was a first step to improve bedside diagnosis of meningococcal infection in Niger, a country within the meningitis belt (10,12). This test however does not identify serogroup X.

While NmX is still rare in Europe (13), its increasing importance in the meningitis belt favours the licensing of an efficient diagnosis device against NmX infection as well as ongoing studies toward a NmX polysaccharide-based vaccine (14).

There is thus a need for a method providing the reliable detection of serogroup X of *N. meningitidis*, and especially for a method which is rapid, which preferably does not require well-equipped laboratories with specialized technicians, and also preferably is not expensive, and thus which can advantageously be used in field conditions. There is also a need to provide antibodies which are capable of detecting group X of *N. meningitidis* with high sensitivity and specificity.

The present inventors have unexpectedly obtained polyclonal antibodies, which are highly specific for the capsular polysaccharides of *Neisseria meningitidis* serogroup X and can detect these polysaccharides with an improved sensitivity. These antibodies are inter alia highly suitable for detecting this serogroup in body fluid, without culture, allowing a rapid diagnostic test (RDT) for the detection of NmX isolates. Such a RDT can be used for the diagnosis and surveillance of meningococcal *meningitidis* in the *meningitidis* belt.

According to a first aspect, the present invention is thus directed to polyclonal antibodies, which are specific for the capsular polysaccharides of *Neisseria meningitidis* serogroup X (NmX), especially polyclonal antibodies which are capable of detecting these polysaccharides in solution. These polyclonal antibodies are indeed sufficiently sensitive to detect soluble polysaccharides characteristic of NmX. These polyclonal antibodies according to the invention are thus suitable for the in vitro detection of *Neisseria meningitidis* serogroup X in biological fluids, without requiring any step of culture. The polyclonal antibodies are thus suitable for detecting soluble antigens of NmX, especially in biological fluids.

The polyclonal antibodies according to the invention comprise at least two different antibodies targeting specifically the capsular polysaccharides of NmX, preferably different epitopes of these polysaccharides characteristic of NmX. The polyclonal antibodies of the invention comprise preferably more than 10, 20, 50 or even 100 distinct antibodies, targeting the capsular polysaccharides of NmX.

According to a preferred embodiment of the invention, the polyclonal antibodies as defined are immunoglobulin G (IgG) antibodies. Whereas other types of immunoglobulins may be present, polyclonal antibodies according to the invention are mainly immunoglobulins G, for example more than 80% of the polyclonal antibodies according to the invention are IgG, preferably more than 85%, 90% or 95%, even preferably more than 98% or 99% of the polyclonal antibodies are IgG.

The polyclonal antibodies of the invention can be obtained, for example, by immunization of an animal, preferably a non-human animal. Suitable animals according to this embodiment are chickens or mammals, especially rabbit, mouse, goat, guinea pigs, hamster, horse, rat, alpaca or sheep. According to a most preferred embodiment of the invention, the antibodies are rabbit, horse or alpaca polyclonal antibodies, most preferably rabbit polyclonal antibodies; the polyclonal antibodies are thus isolated from an immunized non-human animal, which is preferably a rabbit, a horse or an alpaca, and most preferably a rabbit. The polyclonal antibodies may be isolated from one or more than one animal; for example the polyclonal antibodies may be a mixture of polyclonal antibodies isolated from 2, 3 or more rabbits, or 2, 3 or more mice. It is also envisaged in the context of the present invention that the polyclonal antibodies be isolated from at least 2 different types of animals, for example isolated from an immunized alpaca and an immunized rabbit.

According to a preferred embodiment of the invention, the polyclonal antibodies may indeed be obtained by immunization of an animal, and preferably of a mammal, with whole NmX bacteria, followed by a purification of the serum isolated from said animal, preferably mammal, by affinity chromatography with capsular polysaccharides of NmX.

According to this embodiment, the animal or mammal to be used for immunization is preferably a non human animal; preferred animals are as disclosed above, inter alia chicken, rabbit, mouse, goat, guinea pigs, hamster, horse, rat, alpaca or sheep.

The NmX bacteria to be used for the immunization step are preferably inactivated before administration to the animals, for example either by heat, chemical or radiation.

With respect to the affinity chromatography step, it is preferably carried out with pure *Neisseria meningitidis* serogroup X capsular polysaccharides as the ligand, i.e. with NmX polysaccharides in the absence of polysaccharides from other bacteria, in the absence of proteins and of nucleic acids.

As disclosed above, according to a preferred embodiment, the polyclonal antibodies of the invention are likely to be obtained by immunization of one or several rabbits, preferably with whole inactivated NmX, followed by affinity chromatography on purified NmX polysaccharides, preferably on a column charged with purified NmX polysaccharides. The NmX polysaccharides can be purified as illustrated in the experimental section, and their purity can be checked as mentioned in the examples below, for example by NMR.

The polyclonal antibodies according to the invention do not cross react with other types of bacteria; especially they do not cross react with *E. coli, H. influenza, S. pneumonia*. The polyclonal antibodies also do not cross react with any serogroup of the *Neisseria meningitidis* other than serogroup X. Inter alia, they do not cross-react with any of the 11 other serogroups identified for *N. meningitidis*, namely serogroups A, B, C, Y, W (previously known as W135), Z, E (previously known as 29E), H, I, K and L.

The polyclonal antibodies of the invention are thus highly specific for the serogroup X of *Neisseria meningitidis* and thus allow the specific detection of this serogroup and allow distinction between this serogroup and any other serogroup. In this respect, it is to be mentioned that the specificity of the polyclonal antibodies of the invention is a feature which is shared by all the antibodies constituting these polyclonal antibodies, i.e. they are all specific for NmX and do not cross react with any other bacteria or any other serogroup of *N. meningitidis*.

By way of contrast, the antibodies against NmX known before the present invention, are not entirely specific for NmX and thus have been disclosed as cross-reacting with other serogroups of *N. meningitidis* (Afssaps report, 25 Nov. 2009, by Dr Natacha Charler-Bret).

Moreover, none of the prior antibodies were validated for the detection of soluble antigens from NmX, being thus much less sensitive than the antibodies of the invention.

The invention is also directed to a diagnostic agent, corresponding to the polyclonal antibodies of the invention, specific for NmX, linked to a detection label. The linkage between the polyclonal antibodies and the detection label can be any sort of linkage, either directly, or indirectly, for example via another molecule or support. The linkage may be a non-covalent linkage, for example based on electrostatic forces, or may be a covalent linkage. According to preferred embodiments of the invention, the polyclonal antibodies, or at least 50% of said antibodies, are linked by a covalent bond to a detection label.

A detection label as used here consists in or comprises preferably a reporter group, selected for example from enzymes, substrates, cofactors, inhibitors, dyes, radioisotopes, luminescent groups, fluorophores, colorimetric indicators, gold particles, latex particles, and biotin. Any other reporter group may also advantageously be used. Such a reporter group allows the revelation of the detection label and thus of the antibodies linked to said detection label. The way of revealing the reporter group is dependent of course on the reporter group.

In the context of the present invention, the polyclonal antibodies, or at least a majority thereof, are preferably linked to gold particles, especially when they are to be used in rapid diagnostic test such as a dipstick test. In this way, they can be visualized on a solid support without difficulty, without the need for specific equipment, and very rapidly.

The polyclonal antibodies according to the invention are indeed specifically suitable for soluble detection of antigens of NmX, thus allowing the specific detection of NmX, i.e. allowing the discrimination of serogroup X from other serogroups.

According to a second aspect, the present invention is thus directed to different methods for detection of NmX, the detection being specific for serogroup X, allowing the discrimination between this serogroup and other serogroups of *Neisseria meningitidis*.

According to a preferred embodiment of said method, the detection is to be made in a biological fluid, inter alia obtained from a patient affected or suspected to be affected by meningitis infection; i.e. without a culture step. Such a method comprises the step of contacting the fluid with polyclonal antibodies according to the invention or with the diagnostic agent of the invention, and the step of determining the presence or absence of NmX antigens in the fluid.

The method as described is preferably to be carried out in vitro or ex vivo. The first step of contacting the fluid with the polyclonal antibodies is thus made in vitro or ex vivo. The polyclonal antibodies are advantageously linked to a detection label, as disclosed above.

The antigens of NmX are polysaccharides of NmX, specifically capsular polysaccharides of NmX. The antigens likely to react with the polyclonal antibodies of the invention are advantageously soluble antigens of NmX present in the biological fluid.

The presence or absence of NmX antigens can be determined by any appropriate means known to the skilled person in the art; this depends mainly on the detection label attached to the polyclonal antibodies of the invention. According to a preferred embodiment, the presence or absence of soluble antigens of NmX can be determined by simple visual inspection, for example of the fluid sample in the presence of the polyclonal antibodies, or by visual inspection of a solid support previously contacted with the biological sample and with the polyclonal antibodies. Alternatively, any other appropriate means can be used, for example in order to quantify the interaction between the polyclonal antibodies and the biological fluid.

According to a preferred embodiment of the method, the second step of determining the presence or absence of NmX is carried out by detection of the presence or absence of a complex, specifically an immune complex, formed between the polyclonal antibodies and the soluble antigens of NmX.

In an embodiment, the method comprises the use of a detection component which is specific for the polyclonal antibodies of the invention, and thus allows the detection of said antibodies, even bound to their targets. As an illustration, if rabbit polyclonal antibodies are used in carrying out the invention, the detection component is for example mouse or goat anti-rabbit antibodies, thus allowing the detection of the presence of the polyclonal antibodies of the invention. According to this embodiment, the antigens of NmX present in the sample are preferably immobilized, such that the detection of the polyclonal antibodies of the invention, after washing steps, is indicative of the presence of NmX antigens.

In another alternative embodiment, the method comprises the use of a detection component which is specific for the NmX antigens, for example such a component may comprise polyclonal antibodies according to the invention. As an illustration, if polyclonal antibodies linked to a detection label are used in the first step of contacting, the same polyclonal antibodies, unlabelled but immobilized on a solid support, can for example be used to detect the presence of the complex between the labeled polyclonal antibodies of the invention and the soluble antigens of NmX.

The method of the invention is to be used for the specific detection of NmX, i.e. the method allows the determination of whether antigens of NmX are present or absent from the biological fluid under consideration, independently of any other serogroups of *Neisseria meningitidis* or any other bacteria likely to be also present in said fluid.

The biological fluid to be used in carrying out the method is any appropriate biological fluid in which antigens of NmX are likely to be found in case of *meningitidis* infection. Appropriate fluids are for example cerebrospinal fluid, blood, serum, urine, joint fluid, pericardial fluid and pleural fluid. The detection means are to be adapted to the fluid considered and to the concentration of NmX antigens likely to be present. Preferred biological fluids are cerebrospinal fluid, blood, serum and urine, and most preferably cerebrospinal fluid.

According to a preferred embodiment, the invention is directed to an in vitro method for diagnosing a *Neisseria meningitidis* serogroup X infection in a subject, comprising carrying out the method as defined above, on a biological fluid sample from said subject. Preferably said subject is affected by *meningitidis* or is suspected to be affected, either because the subject presents some symptoms indicative of *meningitidis*, or because the subject has been in contact with affected persons.

According to this method of diagnosing, the presence of antigens of *Neisseria meningitidis* serogroup X in the sample is indicative of *Neisseria meningitidis* serogroup X infection.

The sample is preferably a sample of a biological fluid as detailed above, and especially a sample of cerebrospinal fluid, a sample of blood or a sample of urine. The volume of the sample may be very small, insofar as the method for diagnosing according to the invention does not require any step of culturing bacteria from said sample, a few mL can be sufficient or even a smaller quantity. For example, the sample is 150 µL of biological fluid when the method of diagnosing is carried out as described in Examples.

The sample used for carrying out the method of the invention has preferably been obtained from the subject under sterile conditions. It is highly preferred that the method is carried out in the hours following the sampling of the fluid. Alternatively, the sample can be stored under sterile conditions, preferably in the cold, until the diagnostic method of the invention is carried out.

According to a third aspect, the present invention is directed to a diagnostic kit for detecting *Neisseria meningitidis* serogroup X. Such a diagnostic kit comprises polyclonal antibodies of the invention, or said polyclonal antibodies linked directly or indirectly, covalently or non-covalently to a detection label, corresponding to a diagnostic agent as defined above. The polyclonal antibodies according to the invention are either in a free, soluble form, or are immobilized on a support.

According to a preferred embodiment, the kit also comprises a means for detecting the production of an immune complex between said antibodies and antigens of NmX. Such means can be of any type, it can be for example antibodies specific for one or the other partner of the immune complex, i.e. either antibodies directed to capsular polysaccharides of NmX, or antibodies directed to the polyclonal antibodies of the kit. Suitable means also comprise any means detecting the formation of a complex on the basis of the properties of the immune complex formed, for example its weight, its size, etc.

According to a preferred embodiment of the diagnostic kit of the invention, the kit is for detecting NmX in a biological fluid sample, without any culture step, especially without bacteria culture. Such a kit can for example be used immediately after sampling, without the usual delay due to the culture in case of serogroup X detection, which was strictly necessary before the present invention.

Adequate biological fluid samples have been detailed above, it includes cerebrospinal fluid, blood, serum, urine, joint fluid, pericardial fluid and pleural fluid. Preferred fluids for the diagnostic kits of the invention are cerebrospinal fluid, blood, serum and urine, and more preferably cerebrospinal fluid.

According to preferred embodiments of the diagnostic kits of the invention, the detection is carried out by immunoassay, taking advantage of an immunological reaction of NmX antigens with the polyclonal antibodies of the invention.

In this respect, any immunoassay can be used in the context of the present invention, to detect antigens of NmX in a biological fluid sample, either in a qualitative (positive or negative) or quantitative (amount measurement) manner. Many different immunoassays have been developed, which are highly adaptable and can be applied to many different formats, depending on the needs of the end user; these different tests are all applicable in the context of the present invention, taking advantage of the high specificity and sensitivity of the polyclonal antibodies according to the invention.

In addition to the antibodies to be used, namely the polyclonal antibodies of the invention, the second feature of an immunoassay is the technology and the system which are to be used to detect the binding of the polyclonal antibodies to the target analyte, namely soluble antigens of NmX.

Originally, the signal from an immunoassay resulted from an enzyme, to be bound to the complex formed by the antibodies and the target antigens, acting on a substrate to yield a colored solution, wherein the intensity of the coloration is indicative of the amount of target antigen in the test solution.

More recently new immunoassays have been developed, compressing the many steps of the previously designed immunoassays into a simplified format for the end user. One of such simplified formats is the nitrocellulose test strip. In this format, binding of the antibody to the target antigen can be directly observed, by the naked eye, due to the accumulation of dyed microbeads that will bind to a specific location on the nitrocellulose yielding a colored line, in case of presence of the target antigens in the solution to be tested.

Other immunoassays have been developed wherein the sensitivity of the assay has been improved, allowing the detection of single molecules in a body sample. To this end, microscopic beads coated with the antibodies are added to the body sample to be analysed, in order to capture the target antigens; the thus formed immunocomplexes are then labeled with an enzymatic reporter capable of generating a fluorescent product (27).

Other classical immunoassays which are well known and can be used in the context of the present invention are radioimmunoassay and Fluorescent Immunoassays. The key variable is the biochemical technique used for detecting the binding of the "detection" antibody, namely the polyclonal antibodies of the invention, and the soluble antigens of NmX.

A modern fluorescent based immunoassay uses as the detection reagent a fluorescent compound which absorbs light or energy at a specific wavelength and then emits light or energy at a different wavelength. Recently a number of technical improvements have occurred that has enabled the implementation of high sensitivity fluorescent immunoassay system.

Immunoassays are thus designed in many formats and the skilled person will know how to determine the most suitable immunoassays depending on the sample types including serum, plasma, whole blood, urine, or cerebrospinal fluids.

Preferred immunoassays are those which can be carried out rapidly and those which are extremely sensitive.

Immunoassays which can be advantageously used in diagnostic kits according to the invention are those relying on agglutination. In agglutination tests in the context of the invention, a particle (latex bead or bacterium) is coupled to the polyclonal antibodies of the invention. The resulting particle complex is mixed with the sample of biological fluid to be analyzed; if the target antigen, namely soluble antigens of NmX is present in the sample, it cross-links the particles, producing measurable agglutination.

If results are positive, the biological fluid is serially diluted and tested. Agglutination with more dilute solutions indicates higher concentrations of the target antigen(s), namely capsular polysaccharides of NmX.

Usually, agglutination tests are rapid but less sensitive than many other methods.

A particularly preferred agglutination test is latex agglutination test. This test uses latex particles, coated or coupled with the polyclonal antibodies of the invention. Presence of the polysaccharides of NmX leads to the agglutination of the coated latex particles, which can be visually observed in a few minutes or even less. A kit of the invention according to this embodiment thus comprises the polyclonal antibodies of the invention, coated on latex particles.

According to another embodiment, the diagnostic kits of the invention are based on an enzyme-linked immunosorbent assay (ELISA) test. In ELISA test, the sample potentially comprising antigens of NmX is immobilized on a solid support, usually a polystyrene microtiter plate. After immobilization of the antigens, the polyclonal antibodies of the invention are used as detection antibody, forming a complex with the antigens of NmX, if present. The detection polyclonal antibodies can be directly covalently linked to an enzyme, or can be detected by a secondary antibody, that is linked to an enzyme. Between each addition step, the solid support is treated to remove any non-specifically bound proteins or antibodies. The solid support is developed by adding an enzymatic substrate to produce a signal, generally visually detectable, which indicates the potential presence of NmX antigens in the sample, and if appropriate, the quantity thereof.

In such a case, the polyclonal antibodies present in the kits according to the invention are preferably linked to an enzyme, or the kits comprise antibodies specific to the polyclonal antibodies of the invention and linked to an enzyme. According to a specific embodiment, the kit comprises rabbit polyclonal antibodies according to the invention and goat anti-rabbit antibodies, linked to an enzyme.

According to a specific embodiment, the kit is suitable for use in the Simoa™ (single-molecule array) technology (27). For such a purpose, the polyclonal antibodies according to the invention, used as capture antibodies, are attached to the surface of paramagnetic beads. According to this technology, these beads are then contacted with the sample, potentially comprising soluble NmX antigens. The beads are then washed to remove proteins non-specifically bound and incubated with a detection antibody linked to an enzyme. Such a detection antibody is preferably polyclonal antibodies according to the invention.

In such a case, the kits of the invention according to this embodiment comprises the polyclonal antibodies of the invention linked to beads, preferably paramagnetic beads, as capture antibodies, and also the polyclonal antibodies of the invention linked to an enzyme, as detection antibodies.

According to still another embodiment, the kits of the invention are suitable for rapid diagnostic tests, especially lateral or vertical flow assays, also known as immunochromatographic assays; more preferably they are conceived as dipstick tests. According to this embodiment, the kit thus comprises the polyclonal antibodies according to the invention, linked to gold particles, as detection antibodies, and also the polyclonal antibodies of the invention not-linked to gold particles immobilized in a specific area of a support, as capture antibodies.

The diagnostic kits of the invention are preferably stable at temperature up to 30° C., preferably up to 45° C. at least.

Many other technologies can be used for the diagnostic tests of the invention and the technologies detailed above are for illustrative purpose only.

Depending on the technology to be used for demonstrating the presence of soluble antigens of NmX in the sample with the polyclonal antibodies of the invention, several additional components can be present in the diagnostic kits as described.

According to a preferred embodiment, the kit of the invention comprises in addition a solid support, on which the polyclonal antibodies of the invention, either linked to a detection label or not, may be immobilized, but not necessarily. The diagnostic kit according to the invention may comprise inter alia a microtiter plate, a diagnostic platform, a nitrocellulose membrane or a miniaturized lateral or vertical flow device.

With respect to the diagnostic platform, such a platform may comprise a membrane, for example a charged membrane, plastic, beads, strips, microtiter wells, microchannels or a combination thereof.

The kits of the invention may comprise an immunochromatographic test strip, miniaturized lateral or vertical flow device, or enzyme-linked immunosorbent assay platform.

Depending on the technology to be used for revealing the potential presence of soluble antigens of NmX, the kits of the invention may also comprise a fluid receiving zone or chamber, preferably in or on the diagnostic platform.

The skilled person will adapt without difficulty the components of the kits, depending on the chosen technology for detecting the presence of soluble polysaccharides of NmX in the biological fluid sample to be tested.

According to a preferred embodiment of the invention, the diagnostic kit allows the detection by enzyme-linked immunosorbent assay at subfemtomolar concentration, for example at a concentration of 1 fM or below, for example of at a concentration of 0.5 fM of polysaccharide of NmX in the sample, or even below. In order to obtain such a low detection concentration, the technology to be chosen for the detection of soluble antigens of NmX is preferably the Simoa™ technology as detailed above. The advantages of this high sensitivity are that a very early detection can be carried out, for example before apparition of any symptom. This is especially useful for detecting infection in persons who have been in contact with affected patients.

According to a particularly preferred embodiment, the present invention is directed to a dipstick diagnostic test for NmX. Such a test comprises a membrane, which is preferably a nitrocellulose membrane. Such a membrane advantageously comprises the following zones:

a. a first zone comprising the polyclonal antibodies of the invention, linked directly or indirectly, covalently or non covalently to a detection label;

b. optionally a control zone comprising an immobilized control polypeptide,
c. a capture zone comprising immobilized polyclonal antibodies according to the invention, as capture antibodies.

The biological fluid sample to be tested is brought into contact with one extremity of the membrane. The sample then migrates along the membrane, either vertically or laterally depending on the system, first through the 1$^{st}$ zone where soluble antigens of NmX, if present in the sample, will bind to the polyclonal antibodies. As the sample flows through the Capture zone, the immune complex, formed by the polyclonal antibodies and the antigens of NmX, will bind to the immobilized polyclonal antibodies, provided that soluble antigens of NmX are present in the sample, thus capturing and immobilizing the detection label linked to the polyclonal antibodies in a specific area of the membrane. Otherwise, no detection label is captured by the capture antibodies. As the sample flows through the control zone, the polyclonal antibodies linked to the detection label will bind to the control zone, irrespective of whether they are bound to soluble antigens of NmX.

It is thus imperative that the sample flows through the first zone before flowing through the capture or control zone; the respective disposition of the capture and control zones is not critical.

According to a preferred embodiment, the first zone as defined above comprises the diagnostic agent as defined in the context of the present invention. It is particularly preferred that the polyclonal antibodies according to the invention are conjugated, preferably by covalent binding, to gold particles, for the detection.

With respect to the control zone, the immobilized control polypeptides are advantageously control antibodies, especially antibodies capable of recognizing the polyclonal antibodies of the first zone irrespective of whether said antibodies are conjugated to gold particles, and irrespective of whether these antibodies are linked to their specific antigen, namely linked to polysaccharides of NmX. According to a preferred embodiment, when the polyclonal antibodies according to the invention have been obtained by immunization of a specific mammal, for example by immunization of a rabbit, the control polypeptides are antibodies specifically directed to antibodies of said mammal, for example they are goat or mouse anti-rabbit antibodies. Of course, depending on the polyclonal antibodies used in the first zone of the membrane, the control polypeptides are to be adapted in order to recognize these antibodies.

Regarding the capture zone of the membrane, it comprises polyclonal antibodies according to the invention, which are not linked to the detection label of the antibodies present in the first zone. Preferably they are not linked to any detection molecule of any type.

Suitable means for immobilizing the control polypeptides of the control zone and the antibodies of the capture zone are well known to the skilled man. By definition, the antibodies of the first zone are not immobilized on the membrane and constitute a mobile phase.

The different zones of the dipstick test are preferably distinct and not overlapping before use of the dipstick.

The dipstick test of the invention is simple, convenient, quick and concise operation and does not require special equipment and facilities as well as professional training. Furthermore, the dipstick has clear and easy-identity results, simple operation and easy popularization, is applicable to matrixes, field tests of emergency on a large scale and the study of epidemiology and can aid in the infection diagnostics.

The diagnostic test or dipstick test according to the invention is preferably characterized by a sensitivity (Se) of at least 90%, preferably at least 92%, at least 93% or at least 94%. Preferably the 95% confidence interval for the sensitivity is between 86% and 98%. This sensitivity is preferably obtained in case of diagnostic in sample of cerebrospinal fluid.

According to another preferred embodiment, the diagnostic kit or test according to the invention has a specificity (Sp) which is at least 90%, preferably at least 95%, at least 98% or at least 99%, especially when applied on field conditions. Preferably the 95% confidence interval for the specificity is between 99% and 100%. This specificity is preferably obtained in case of diagnostic in sample of cerebrospinal fluid.

It is preferred that the performance of the dipstick test of the invention is a sensitivity of at least 86% with a specificity of at least 98%, preferably a sensitivity of at least 92% with a specificity of at least 99%.

It is also preferred that the diagnostic kit as described, especially dipstick, has one or several of the following parameters:
 a positive likelihood ratio comprised between 32 and 8252; and/or
 a negative likelihood ratio comprised between 0.03 and 0.15; and/or
 a positive predictive value comprised between 0.96 and 1; and/or
 a negative predictive value comprised between 0.95 and 0.99 and/or
 a diagnostic odd ration comprised between 379 and 118420.

The positive likelihood ratio LR+(LR+=Se/[1−Sp]) indicates how many times a positive result is more likely to be observed in specimens with the target disorder (NmX infection) than in those without the target disorder. The negative likelihood ratio LR−(LR−=[1−Se]/Sp) indicates how many times a negative result is more likely to be observed in specimens with the target disorder (NmX infection) than in those without the target disorder.

The more accurate test is, the more LR differs from 1. LR+ above 10 and LR− below 0.1 are considered convincing diagnostic evidence.

The diagnostic odds ratio (DOR), defined as the ratio of the odds of positive test results in specimens with the target disorder (NmX infection) relative to the odds of positive test results in specimens without the target disorder, is calculated as follows: DOR=(Se/[1−Se])/([1−Sp]/Sp).

The DOR does not depend on prevalence and its value ranges from 0 to infinity, with higher values indicating better discriminatory test performance.

The positive predictive value (PPV) represents the proportion of test-positive specimens that truly present the target disorder (NmX infection), while the negative predictive value (NPV) represents the proportion of test-negative specimens that truly do not present the target disorder:

PPV=(Prev×Se)/(Prev×Se)+([1−Prev]×[1−Sp]) and

NPV=([1−Prev]×Sp)/([(1−Prev)×−Sp]+[Prev×(1−Se)]).

"Prev" is the prevalence of the target disorder (NmX infection) in the population of specimens to which the test is applied.

According to another preferred embodiment of the invention, the diagnostic kit or test has a detection limit of the NmX capsular polysaccharide of around 1 ng/mL, preferably of less than 1 ng/mL, especially in case of use of the Simoa™ technology.

According to another preferred embodiment of the invention, the diagnostic kit or test has a detection limit of NmX bacteria of around $10^5$ CFU/ml.

According to another aspect, the present invention also concerns the use of a diagnostic kit or test as defined above, preferably for the in vitro diagnostic of NmX infection in the biological sample of a subject. Said subject may be suspected of meningitis infection, or may have been in contact with infected patients.

The biological sample which can be used in this context is as defined in the other aspects of the invention, inter alia it is preferably a sample of cerebrospinal fluid, urine, serum or blood. The other preferred embodiments are also as detailed above, regarding other aspects of the invention.

According to a further aspect, the present invention is also directed to a method for producing the polyclonal antibodies of the invention, i.e. which are highly specific for and sensitive to polysaccharides of NmX and which can be used for the detection of NmX without culture. Such a method according to the invention comprises preferably the following steps:
 a. immunizing an animal host with an immunogenic composition comprising whole *Neisseria meningitidis* serogroup X bacteria; and
 b. isolating from the serum of said animal host, the antibodies specific for *Neisseria meningitidis* serogroup X, by affinity chromatography with capsular polysaccharides of *Neisseria meningitidis* serogroup X.

According to a preferred embodiment of said method, the animal to be used for immunization at step a) is a non human animal. Preferably it is a mammal, or a chicken. Preferred mammals have been detailed in the context of other embodiments of the invention; most preferred mammals are horse, alpaca and rabbit, preferably rabbit.

According to a preferred embodiment of the invention, the immunization step is carried out with whole inactivated bacteria. Inactivation is preferably carried out by heat, but other means to inactivate NmX are well known to the skilled person in the art.

With respect to the second step, the isolation from the serum of said animal host, of the antibodies specific for *Neisseria meningitidis* serogroup X, is carried out with purified capsular polysaccharides of NmX, preferably loaded on a chromatography column.

The method of the invention is not limited to the steps described above and may comprise supplemental steps, either carried out before, after or between the steps described. The method may inter alia comprise a further step of isolation of the immunoglobulins G from the serum of said animal host. This isolation step can be carried out for example by an affinity chromatography with protein G ligands as detailed in the experimental section. This type of isolation is well known to the skilled person and can be carried out without difficulty. Preferably, such a step of isolation of IgG is carried out before the isolation step b) of the method, i.e. between steps a) and b).

With respect to the purification of the polysaccharides of NmX, to be used in the chromatography column, it is preferably conducted until a purity of at least 95%, preferably at least 99% before being loaded on a column for the affinity chromatography. Step b) thus consists in a chromatography carried out on immobilized polysaccharides of NmX having a purity of at least 95%, preferably at least 99%.

As illustrated in the experimental section, the isolation of polyclonal antibodies of the invention is performed by affinity chromatography in two steps. First the animal serum is passed through a Protein G column and is eluted with an appropriate solution, for example glycine-HCl 0.1M, pH 2.7. The fractions are then recovered in a buffer, preferably Tris-HCl. The pooled fractions are then passed through a capsular NmX polysaccharide affinity chromatography, obtained by chemical coupling of the resin of the chromatography column and the capsular polysaccharides, and then eluted with an appropriate solution.

The eluted fractions can then be tested by Elisa against purified capsular polysaccharides of NmX and whole inactivated NmX bacteria, for verification.

The present inventors have found that this method provides polyclonal antibodies, specific for the capsular polysaccharides of NmX, not cross reacting with the other serogroups of meningococci and not cross reacting with other bacteria, especially when the animal is rabbit.

Moreover, the inventors have confirmed that such polyclonal antibodies can be reproducibly obtained by repeating the method on another animal. The polyclonal antibodies thus obtained have almost identical properties, confirming the reproducibility of the method.

LEGENDS OF FIGURES

FIG. 1. Dot blotting analysis of rabbit sera. Sera from two rabbits prior to immunization (day 0) and 7 days after injection of the third dose of NmX strain 19504 (day 28) were used at 1:1000 dilutions in immunoblotting. Four meningococcal isolates were spotted at $2.10^5$ colony forming units, CFU/mL (1: strain 19404, 2: strain 23557, 3: strain 24196, 4: strain 24287).

Figure 2:
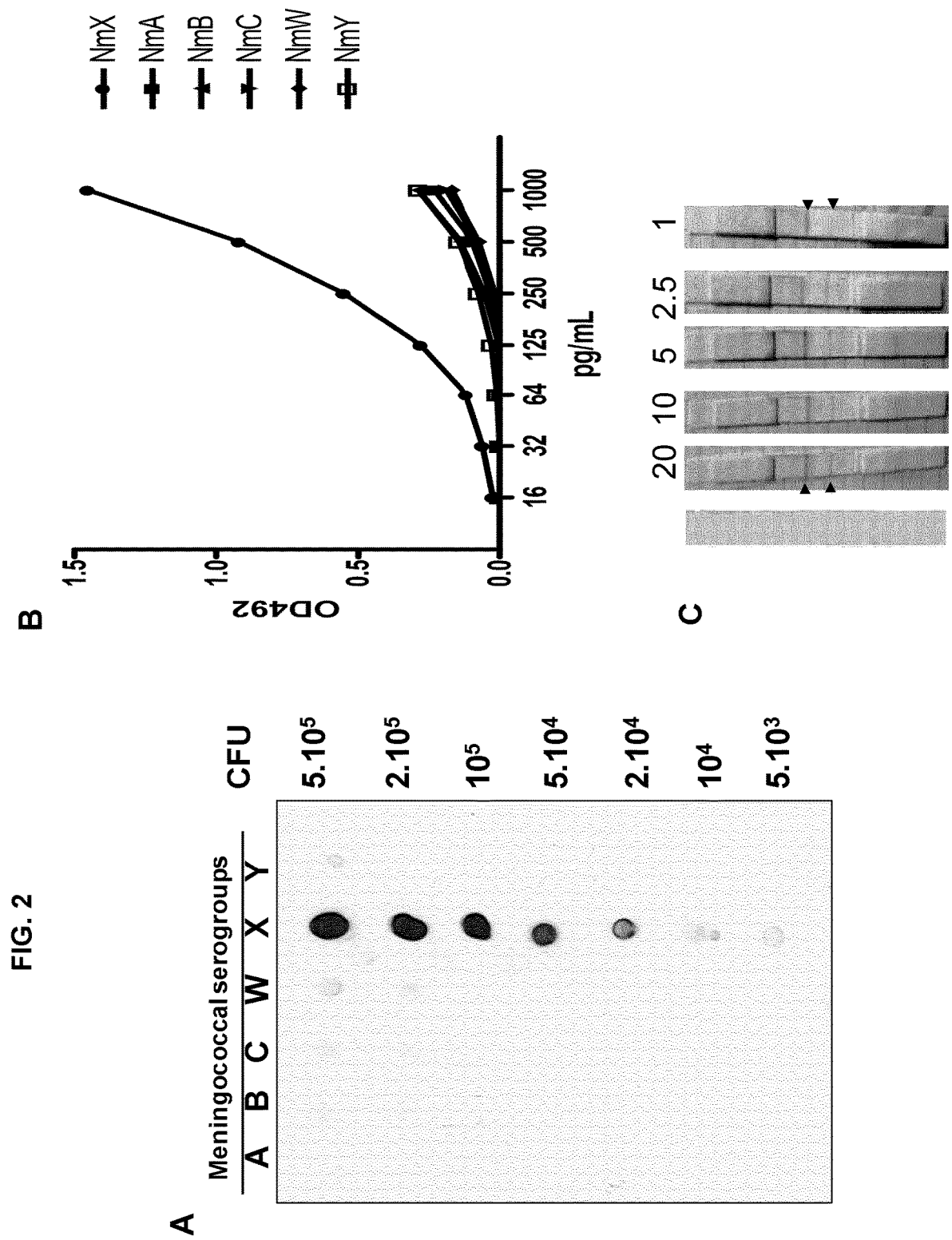

FIG. 2. Specific recognition of the purified rabbit anti-cpsX IgG antibodies. (A) Dot blotting analysis against whole bacteria. Serogroups are indicated above the dots and amounts of loaded bacteria in each spot are indicated on the right (in colony forming units, CFU). Antibodies were used at a final concentration of 500 pg/mL. (B) ELISA analysis using coated purified capsular polysaccharide for serogroups A, B, C, Y, W and X (Table 1). Data are expressed as OD 492 nm absorption for each concentration of antibodies (in pg/mL). Data correspond to the means of two independent experiments. The corresponding serogroups are indicated on the right. (C) Detection cut-off value for purified cpsX. The amounts are indicated in ng above each dipstick. A dipstick, before use, is shown on the left. The upper two arrows indicate the capture control line corresponding to the goat anti-rabbit IgG. The lower two arrows indicate the capture line corresponding to the anti-cpsX-specific IgG (cpsX line).

Figure 3:
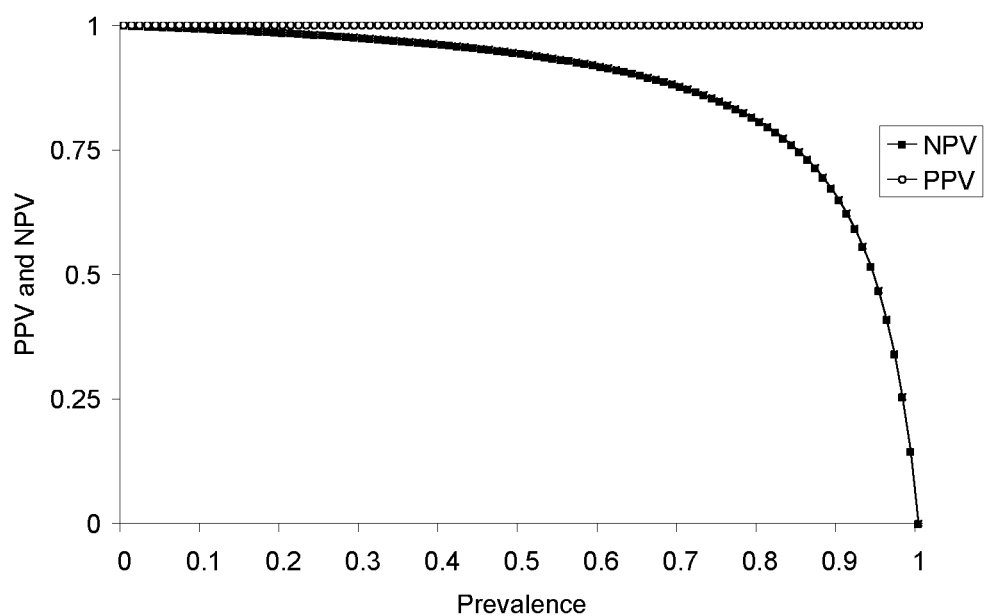

FIG. 3. Predictive values for N. meningitidis diagnosis. Positive Predictive Values and Negative Predictive Values (PPV and NPV, respectively) for the diagnosis of NmX were calculated according to a disease prevalence ranging between 0 and 100%.

Figure 4A:
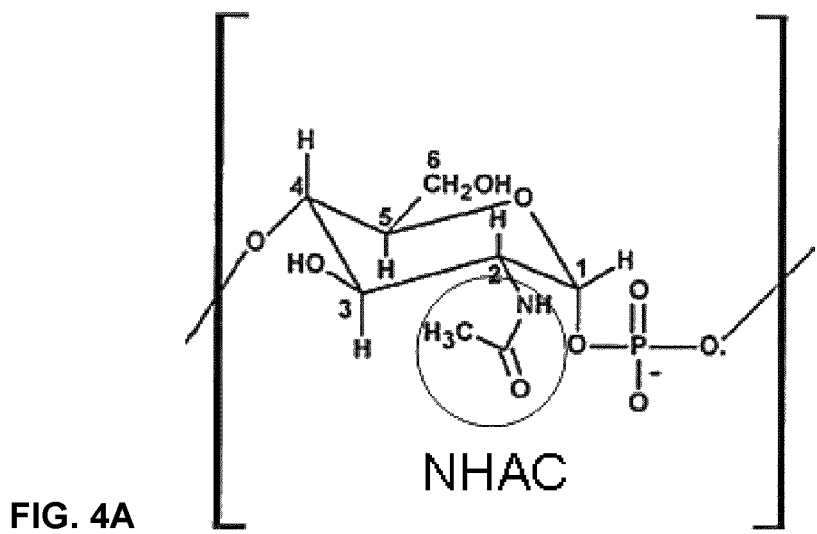
Figure 4B:
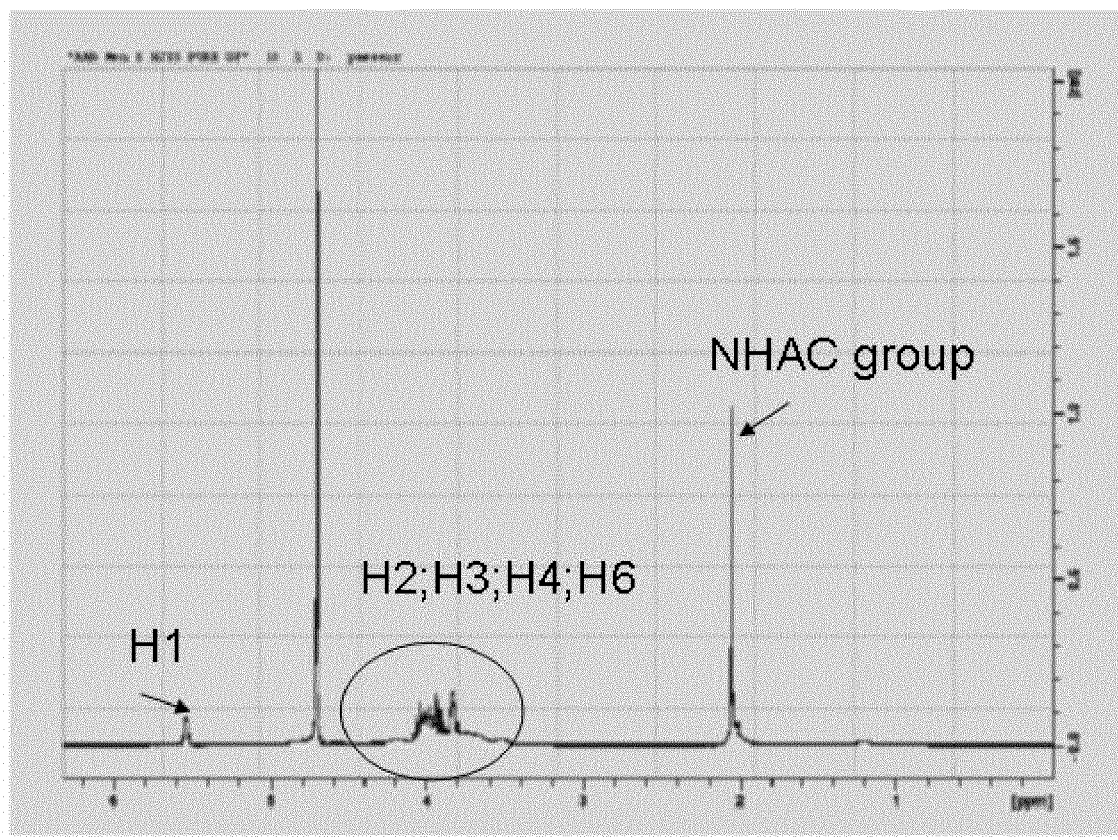

FIG. 4. FIG. 4A: structure of the capsular polysaccharide of meningococci serogroup X: homopolymer of 1ç4-linked N-acetyl-D-glucosamine 1-phosphate. Fig. B: 1H NMR spectrum recorded on a Bruck Avance 400 spectrometer type, with a frequency of 400 MHz. The sample was dissolved in deuterium oxide ($D_2O$). The chemical shifts (δ) are expressed in parts per million (ppm) and the reference used is the 4,4-dimethyl-4-silapentane 1-sulfonic acid (DSS). The coupling constants are given in Herz (Hz). The peaks are indicated according to the position (1 to 6) on the repeated units of the cpsX (see FIG. 4A).

Figure 5:
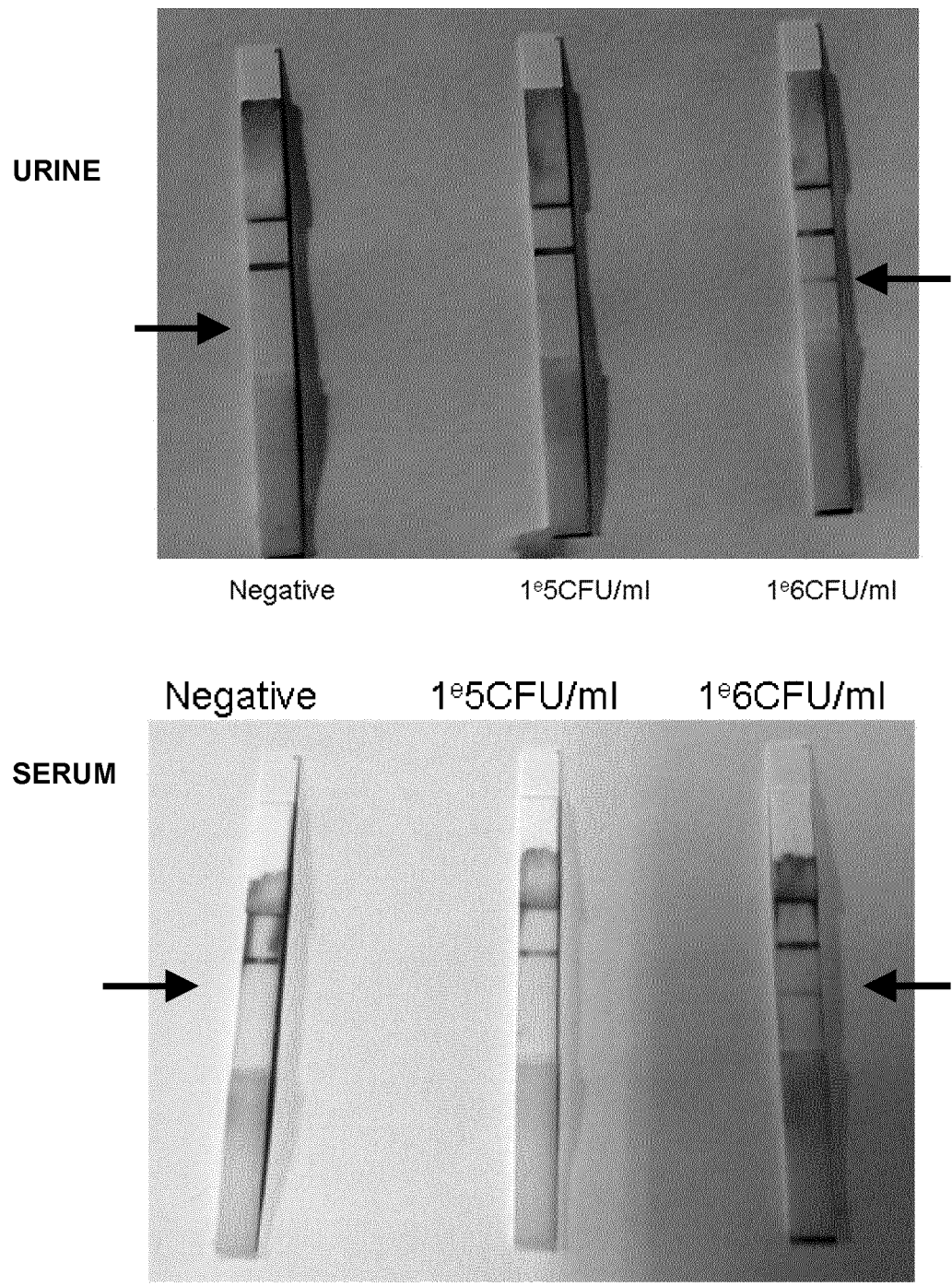

FIG. 5. Detection of meningococci serogroup X in urine and serum using the serogroup X dipstick. The dipsticks disclosed in example 2 were used to detect NmX on urine samples (above) and serum sample (below) at different concentrations of meningococci, namely at 0 CFU/mL (labeled "negative" on the left side), at $10^5$ CFU/mL (middle) and at $10^6$ CFU/mL (right side). The detection line is indicated by an arrow.

EXAMPLES

The inventors have developed and evaluated a new rapid diagnostic test (RDT) for detecting the capsular polysaccharide (cps) antigen of this emerging serogroup. Whole inactivated NmX bacteria were used to immunize rabbits. Following purification by affinity chromatography, the cpsX-specific IgG antibodies, were utilized to develop a NmX-specific immunochromatography dipstick RDT. The test was validated against purified cpsX and meningococcal strains of different serogroups. Its performance was evaluated against PCR on a collection of 369 cerebrospinal fluid (CSF) samples obtained from patients living in countries within the meningitis belt (Cameroon, Côte d'Ivoire and Niger) or in France. The RDT was highly specific for NmX strains. A cut-off of $10^5$ CFU/mL and 1 ng/mL was observed for the reference NmX strain and purified cpsX, respectively. Sensitivity and specificity were 94% and 100%, respectively. A high agreement between PCR and RDT (Kappa coefficient of 0.98) was observed. The RDT test gave a high positive likelihood ratio and a low negative likelihood (0.07) indicating almost 100% probability to declare disease or not when the test is positive or negative, respectively. This unique NmX-specific test could be added to the available set RDT tests for the detection of meningococcal meningitis in Africa as a major tool to reinforce epidemiological surveillance after the introduction of the NmA conjugate vaccine.

Example 1: Materials and Methods

Bacterial Strains and Samples

N. meningitidis isolates used in this study were isolates from cases of meningococcal disease (see Table 1 for details). Bacteria were cultured on GCB medium (GC Agar Base, Difco, Detroit Mich., USA) supplemented with Kellogg supplements (15). The serogroup was determined by agglutination with serogroup-specific antisera according to the standard procedure (16). Further phenotyping (serotyping and serosubtyping) was performed using monoclonal antibodies against the meningococcal proteins PorA and PorB as previously described (17). The cerebrospinal fluid (CSF) samples tested in this study corresponded to suspected bacterial meningitis cases. They were obtained from the National Reference Laboratories for Meningococci located at the Institut Pasteur of Côte d'Ivoire and at the Institut Pasteur, Paris, France, as well as from the Centre de Recherche Médicale et Sanitaire (CERMES) in Niamey, Niger, and from the Centre Pasteur of Garoua, Cameroon. These samples were received in the frame of these centres' mission for the surveillance of meningococcal diseases in the corresponding countries under approvals from the internal board of the Institut Pasteur to collect, characterize and use these samples that are all anonymized.

The PCR analysis of these samples was used as a reference method to detect *N. meningitidis*, *Streptococcus pneumoniae* and *Haemophilus influenzae*, as well as to genogroup meningococcus-positive specimens. PCR conditions and primers were as previously described (8). Culture was not used as it has been constantly shown to be less sensitive than PCR (26). Culture data were available only for 26 of the 369 tested CSF samples.

TABLE 1

Strains used in the study and their characteristics

| Strain reference | Serogroup:serotype/serosub-type |
|---|---|
| 21525* | A:4:P1.9 |
| 21526 | A:4:P1.9 |
| 19256 | B:NT:P1.5, 2 |
| 19257 | B:2a:P1.5, 2 |
| 19324 | B:2b:P1.5, 2 |
| 21721* | B:NT:P1.4 |
| 22733 | B:15:P1.4 |
| 22590 | B:14:P1.7, 16 |
| 22644 | C:15:P1.7, 16 |
| 22639 | C:2a:P. 5 |
| 20137 | C:2b:P1.5, 2 |
| 19008 | C:2a:P1.5, 2 |
| 20134 | C:NT:P1.10 |
| 19456 | Y:14:NST |
| 19336* | Y:NT:P1.5 |
| 19995* | W:2a:P1.5, 2 |
| 19481 | W:NT:P1.5 |
| 19836 | W:NT:P1.6 |
| 19383 | E:NT:P1.5, 2 |
| 19504* | X:NT:P1.5, 2 |
| 24196 | X:4:P1.12 |
| 24287 | X:4:P1.16 |
| 23557 | X:NT:P1.5 |

NT: Nontypeable,
NST: Nonsubtypeable
*Strains that were used for capsular polysaccharide purification Purification of the Capsular Polysaccharide from NmX The capsular polysaccharide of serogroup X (cpsX, see FIG. 4A for structural definition) was purified from the NmX strain, 19504 (that gave the highest yield when cultured on GCB medium with Kellogg supplements), by the CETAVLON extraction method as previously described (18). Briefly, bacteria (1 L) at late-logarithmic phase of growth were formaldehyde-inactivated (1% v/v) and then treated with CETAVLON (0.1% w/v) (Sigma Aldrich, France). After centrifugation, the pellet was dissolved in cold aqueous $CaCl_2$ (0.9M). The solubilised materials were cleared by precipitation in 25% aqueous ethanol and the remaining supernatant was precipitated by 80% aqueous ethanol. The pellet was dissolved in phosphate buffer ($Na_2HPO_4$, $NaH_2PO_4$, 0.2 M) and treated with Dnase and Rnase followed by proteinase K treatment (Sigma Aldrich, France) and cold phenol extraction. The extract was extensively dialyzed against distilled water and lyophilized to obtain the crude capsular polysaccharide. Ten mg of the preparation were dissolved in 2 mL of phosphate buffer $K_2HPO_4$, $KH_2PO_4$ (0.05 M), pH 7, and purified by gel filtration on a Biosep-SEC-53000 column (300×21.2 cm, Phenomenex, France) that was equilibrated with the same buffer. Elution was carried out with the same phosphate buffer at 5 mL/min, and monitored at 214 nm and 280 nm. The void volume fractions containing cpsX in the high molecular-weight range were pooled and dialyzed against distilled water at 4° C., using a dialysis membrane with a cut-off size of 10K-15K, and the residue was lyophilized. The yield was about 20 mg/L of culture. The profile of the purified cpsX was checked by proton nuclear magnetic resonance ($^1H$ NMR) (FIG. 4B) as previously described (19). CpsA, cpsB, cpsC, cpsY and cpsW were similarly purified from five strains of serogroups A, B, C, Y and W (strains 21524, 21721, 22639, 16366 and 19995 respectively, Table 1).

Rabbit Immunization and Purification of Specific Anti-cpsX IgG Antibodies

Two New Zealand White female rabbits (3 kg) were immunised intravenously three times with doses of 1 mL of a suspension of $10^9$ colony forming units (CFU) of freshly heat-inactivated Nmx strain 19504 (30 min at 56° C.), at day 0, 7 and 21. Sera were taken before immunization and at day 28 after the first injection to evaluate the immune response by ELISA (see below). Dot blotting with rabbit sera (1:1000 serum dilution) was performed using Amersham ECL kits (GE Healthcare Life Sciences Velizy-Villacoublay, France) as previously described (20). Rabbit immunisation was performed according to the European Union Directive 2010/63/EU (and its revision 86/609/EEC) on the protection of animals used for scientific purposes. The inventors' laboratory has the administrative authorization for animal experimentation (Permit Number 75-1554) and the protocol was approved by the Institut Pasteur Review Board that is part of in the Regional Committee of Ethics of Animal Experiments of the Paris region (CETEA 2013-0190).

IgG antibody purification was performed by affinity chromatography in two steps. First, the rabbit's sera were passed through a HiTrap Protein G HP column (GE Healthcare, France) and eluted with glycine-HCl 0.1 M pH 2.7. Fractions of 1 mL were recovered in 50 μL of Tris-HCl buffer (1 M, pH 9). Fractions were tested for protein content by measuring their absorbance at 280 nm. Pooled fractions were passed through a cpsX affinity column obtained by chemical coupling of the amine functions of the CarboxyLink resin and the phosphate functions from cpsX, according to manufacturer recommendations (Thermo Scientific, Rockford, Ill. USA). The eluted fractions were tested by ELISA against purified cpsX and whole inactivated NmX bacteria. To do so, ELISA wells were coated overnight with 100 μL of a solution containing 2 μg/mL of purified cpsX or 100 μL of a bacterial suspension of $3.10^8$ bacteria/mL (NmX strain 19504). The purified antibodies (at a 500 pg/ml concentration) were tested against serial dilutions of bacteria from serogroup A, B, C, Y, W and X in a dot blot experiment, and serial dilutions of the antibodies were then tested in ELISA on counterpart coated cps at 2 μg/mL concentration.

Production and Validation of a RDT Against NmX

A one-step vertical flow immune-chromatography dipstick was set up using purified cpsX-pAbs that were conjugated to gold particles (British Biocell International, Cardiff, UK) as previously described (21). Unconjugated cpsX-pAbs were used as capture antibodies and goat anti-rabbit IgG (ICN Biomedicals, Aurora, Ohio, United States) were used as control antibodies. Both types of antibodies were sprayed onto nitrocellulose (Schleicher & Schuell Bioscience, Ecquevilly, France) at 2 μg and 1 μg per line centimeter respectively. For the test evaluation, dipsticks were dipped, for a 10-15 min period at room temperature, in 100 μL of PBS containing bacterial suspensions or CSF samples.

Data Analysis

Sensitivity (Se), specificity (Sp), positive predictive value (PPV) and negative predictive value (NPV) were calculated using a 2×2 contingency table. The positive likelihood ratios LR (LR$^+$=Se/[1−Sp]) and the negative LR (LR$^-$=[1−Se]/Sp), were also calculated (22). These values give an indication of the likelihood that the sample is positive or negative prior to testing. The diagnostic odds ratio (DOR), defined as the ratio of the odds of positive test results in specimens with NmX on the odds of positive test results in specimens negative for NmX, was calculated as follows DOR=(Se/[1−Se])/([1−Sp/Sp] (23). Finally, the Cohen's kappa (j) statistic was calculated to measure concordance between PCR and RDT (24). K may range from 0 to 1, and a j value higher than 0.8 is thought to reflecting almost perfect.

Example 2: Results and Discussion

Characterization of Rabbit Anti-Meningococcal Serogroup X Rabbit Serum

Following the three dose-immunization regimen with whole NmX bacteria, the rabbit sera were tested in dot blot analysis against spotted bacteria. While no bacteria detection was obtained with control pre-immune sera, a strong detection was obtained with the sera from immunized rabbits (FIG. 1). Sera from the two responding rabbits were pooled and anti-cpsX-specific IgG were purified by affinity chromatography on a NmX cps activated column. Dot plot analysis of the purified IgG response against decreasing numbers of bacteria (from 5×10$^5$ to 5×10$^3$ cells per spot) from serogroups A, B, C, Y, W and X showed that antibodies only recognized serogroup X strain (FIG. 2A). The absence of recognition of the other serogroups (A, B, C, Y and W) was further confirmed independently by ELISA analysis of the antibody response against coated (1 μg/mL) purified cps corresponding to the six serogroups (FIG. 2B).

A dipstick rapid diagnostic test for NmX was produced (see Material and Methods), and its detection limits were established. For the purified cpsX, this limit was 1 ng/mL (FIG. 2C) and was 10$^5$ CFU/mL for NmX bacteria (strain 19504). The cut-off analysis was repeated 3 times with identical findings that were not affected by dipstick storage for 3 weeks at 25° C. The inventors also tested the RDT on a collection of bacterial suspension (Table 1) at 10$^6$ CFU/mL. Only the serogroup X isolates were detectable.

The detection limit of 1 ng CpsX/ml is similar to that of ELISA assays and lower than that of latex agglutination assays (10-100 ng CpsX/ml), explaining the higher specificities and sensitivities of RDTs compared with the agglutination kit.

Use of the NmX Dipsticks on Clinical Samples

The NmX dipstick was tested on a panel of 369 CSF selected from historical collections kept in National Reference Centre/Laboratory from four different countries, differing in terms of meningitis incidence (Cameroon, Côte d'Ivoire, France and Niger). Noticeably, three out of the four laboratories are located in countries within the meningitis belt. The CSF samples corresponded to suspected cases of acute bacterial meningitis. They were characterized by PCR for etiological diagnosis (Table 2). Culture results were only available for 26 samples (8 samples positive for *S. pneumoniae*, 4 positive for *N. meningitidis* (2 serogroup B and 2 serogroup W), 1 positive for *H. influenzae*, 1 positive for *S. agalactiae* and 12 CSF samples were sterile by culture).

Among these isolates, 52% (n=191) were positive for Nm, 8% (n=28) were positive for other bacterial species, namely *S. pneumoniae*, *H. influenzae* and *S. agalactiae*, and 40% (n=150) were negative by PCR for these species. Among the Nm positive CSF, the six meningococcal capsular groups involved in invasive meningococcal infections were represented: group A (n=27), group B (n=8), group C (n=7), group Y (n=2), group W (n=38) and group X (n=92). In addition, 17 CSF samples were positive for Nm by PCR although they were negative for groups A, B, C, Y, W and X. All samples that were negative for NmX by PCR were also negative for this group by the new NmX-specific RDT. Among the 92 CSF positive for NmX by PCR, 86 were also positive by RDT. All the 26 CSF samples with culture data were tested negative by NmX-specific RDT.

This validation under laboratory conditions took place during the epidemic season in the three laboratories located in countries of the meningitis belt. Therefore, the inventors took advantage of the epidemic season and tested the new NmX-specific RDT on all 153 CSF samples that were received in the three laboratories in Cameroon, Côte d'Ivoire and Niger. No NmX was detected by PCR or by RDT in any of the samples. In contrast, several samples were positive by PCR for *S. pneumoniae* (14%), NmW (7%) and *H. influenzae* (3%).

TABLE 2

Results of CSF samples obtained by PCR and by RDT

| PCR | Geographical origins | | | | RDT | | |
|---|---|---|---|---|---|---|---|
| | IP Paris | CP CERMES | IP Côte Garoua | d'Ivoire | Total | NmX$^+$ | NmX$^-$ |
| NmA | 6 | 15 | 6 | 0 | 27 | 0 | 27 |
| NmB | 6 | 0 | 0 | 2 | 8 | 0 | 8 |
| NmC | 7 | 0 | 0 | 0 | 7 | 0 | 7 |
| NmY | 2 | 0 | 0 | 0 | 2 | 0 | 2 |
| NmW | 6 | 10 | 4 | 18 | 38 | 0 | 38 |
| NmX | 7 | 80 | 5 | 0 | 92 | 86 | 6 |
| Nm NG | 0 | 0 | 16 | 1 | 17 | 0 | 17 |
| *S. pneumoniae* | 0 | 0 | 10 | 13 | 23 | 0 | 23 |
| *H. influenzae* | 0 | 0 | 1 | 3 | 4 | 0 | 4 |

TABLE 2-continued

Results of CSF samples obtained by PCR and by RDT

| | Geographical origins | | | | RDT | | |
|---|---|---|---|---|---|---|---|
| PCR | IP Paris | CP CERMES | IP Côte Garoua | d'Ivoire | Total | NmX⁺ | NmX⁻ |
| S. agalactiae | 1 | 0 | 0 | 0 | 1 | 0 | 1 |
| Negative* | 10 | 0 | 77 | 63 | 150 | 0 | 150 |
| Total | 45 | 105 | 119 | 100 | 369 | 86 | 283 |

*PCR Negative for N. meningitidis, S. pneumoniae and H. influenzae
CSF: cerebrospinal fluid;
RDT: Rapid Diagnostic test;
IP, Institut Pasteur;
CP: centre Pasteur;
Nm: Neisseria meningitidis;
NG: non groupeable Performance of the NmX-Specific RDT: Sensitivity, Specificity, Likelihood Ratios, and Predictive Values RDT data showed a good correlation with PCR data, indicating a Kappa correlation coefficient of 98%. The sensitivity, specificity and 95% CI (confident interval) data of the RDT obtained for the documented 369 CSF samples are summarized in Table 3. The specificity of RDT for CSF infected by NmX was 100%, while the sensitivity reached 94%. Calculating the positive likelihood $LR^+$ and DOR was not feasible due to a Sp value of 100%. $LR^+$ and DOR values were therefore calculated using a value for the specificity that corresponded to the lower 95% confidence interval for specificity (0.99) (Table 3).

TABLE 3

Performance of the RDT for NmX

| Test parameter | Value | 95% confidence interval |
|---|---|---|
| Sensitivity (Se) | 0.94 | 0.86 to 0.98 |
| Specificity (Sp) | 1 | 0.99 to 1 |
| Positive Likelihood ratio (LH⁺)* | 94 | 32 to 8252 |
| Negative Likelihood ratio (LH⁻) | 0.07 | 0.03 to 0.15 |
| Positive predictive value (PPV) | 1 | 0.96 to 1 |
| Negative predictive value (NPV) | 0.98 | 0.95 to 0.99 |
| Diagnostic odd ratio (DOR)* | 1567 | 379 to 118420 |

Dividing by zero; the values of LH⁺ and DOR were calculated using a value for specificity that corresponded to the lower 95% confidence interval (0.99).

The prevalence of NmX among the 369 tested CSF was 25%. Therefore, the NPV and PPV are given in Table 3 under this prevalence value. However, the tested samples were selected from the collections of the participating laboratories and may not reflect the real prevalence of the disease. Moreover, the frequency of NmX meningitis may also vary across time and countries within the meningitis belt and elsewhere. We therefore calculated the negative and positive predictive values (NPV and PPV) according to a prevalence varying from 0 to 100%, using the Se and Sp obtained from the CSF samples in this study (FIG. 3).

Discussion

Reliable tests for the identification of cases of meningococcal meningitis and serogroup-determination are crucial to ensure proper individual (case-by-case) as well as collective management of cases and epidemiological surveillance. Culturing N. meningitidis may frequently fail due to early antibiotic treatment and fragility of this bacterial species (25). During the last two decades, PCR-based non-culture methods have been developed, enabling a significant improvement of the management and surveillance of bacterial meningitis (26). PCR-based methods require specific laboratory equipment and trained staff and can not be used as a bedside method (i.e. for physicians to make a decision on individual treatment). Nevertheless, the PCR technology was implemented in several reference laboratories located in countries within the African meningitis belt (26). However, PCR may not be sufficiently set to ensure country-wide surveillance, especially in populations leaving in remote areas. Other tests, such as the currently available latex agglutination kits, require trained staff and an unbroken cold chain for storage and distribution of the kits. The recent implementation of RDT for meningococci of serogroups A, C, Y and W was a major breakthrough for individual diagnosis and for surveillance of meningococcal diseases in the African meningitis belt (12). These tests are stable at temperature up to 45° C. at least. They are easy to use and to interpret in the absence of extensive training, and therefore are adapted for bedside use. The emergence of meningococcal isolates of serogroup X urged the development of a RDT test for this serogroup to complete the current RDT tools. We first analyzed the inherent quality of such a serogroup X specific test. The specificity and sensitivity parameters were evaluated under laboratory conditions using a selected panel of relevant CSF samples. The good quality of the new RDT was reflected by its high sensitivity and specificity for NmX with a very high likelihood ratio for positive test (Table 3). The inventors also evaluated its usefulness that depends not only on the quality of the test but also on the prevalence of the NmX meningitis in the tested population. The prevalence of NmX within the panel of CSF samples that was used to evaluate the RDT specificity and sensitivity was 25.7%. It may not properly reflect the real prevalence of NmX in areas at risk. Usefulness is usually evaluated using two parameters, the PPV and NPV. When NmX prevalence was forced to vary between 0 and 100%, the PPV remained stable at 1 indicating that the test remained highly proficient in ruling-in a case. Moreover, the NPV retained high values when the prevalence of NmX was very low. In addition, the test remained proficient (NPV of 0.95 or higher) if this prevalence increased to 50%. These considerations seem realistic and reflect the current epidemiological situation in the meningitis belt after the introduction of MenAfriVac™ that was associated with significant decrease of NmA (9). Indeed, the small scale prospective use of the new RDT in the three centres located in this area (Abidjan, Garoua and Niamey), which is disclosed herein, suggests, on the basis of the sensitivities of RDT and PCR (that are less than 100%) that NmX may be present albeit not as a dominating pathogen. In contrast, NmW was the most frequently isolated Nm species, while most cases were associated to *S. pneumoniae*. However, a large-scale multi-site prospective study comparing PCR and all the available RDT (A, C, Y, W, Y and X) is warranted in the future. The new RDT described here will be crucial in vaccination decision making to implement large scale vaccination with the available broad serogroup coverage vaccine that can target NmX (5) or with NmX-specific vaccines under development (14).

Example 3: Detection of Meningococci Serogroup X in Urine and Serum Using the Serogroup X Dipstick Non-infected urine samples and serum samples were spiked with *Neisseria meningitidis* strain of serogroup X (LNP19504) at a final concentration of $10^5$ and $10^6$ CFU/ml; this technique is indeed frequently used for validation of kits for bacterial detection, including kits for *N. meningitidis* detection as the sensitivity data obtained with spiked samples are known to correlate well with sensitivity data obtained on corresponding bodily fluids of infected patients. These samples were then tested by the dipstick that has been previously described in example 2 to detect meningococcal serogroup X (see also 28).

As shown in FIG. 5, serogroup X was detectable for both concentrations in the urine and no band was detectable in non infected urine. These data are similar to those obtained in CSF samples in example 2.

In the serum, serogroup X was detected at the concentration of $10^6$ CFU/ml but not at $10^5$ CFU/ml suggesting lower sensitivity in serum.

These results demonstrate the feasibility of diagnosing *N. meningitidis* infection in serum and urine samples of individuals to be tested.

REFERENCES

1. Rosenstein N E, Perkins B A, Stephens D S, Popovic T, Hughes J M. 2001. Meningococcal disease. N Engl J Med. 344: 1378-1388.
2. Harrison L H, Pelton S I, Wilder-Smith A, Hoist J, Safadi M A, Vazquez J A, Taha M K, LaForce F M, von Gottberg A, Borrow R, Plotkin S A. 2011. The Global Meningococcal Initiative: recommendations for reducing the global burden of meningococcal disease. Vaccine. 29: 3363-3371.
3. Harrison L H, Trotter C L, Ramsay M E. 2009. Global epidemiology of meningococcal disease. Vaccine. 27 Suppl 2: B51-63.
4. O'Ryan M, Stoddard J, Toneatto D, Wassil J, Dull P M. 2014. A multi-component meningococcal serogroup B vaccine (4CMenB): the clinical development program. Drugs. 74: 15-30.
5. Hong E, Giuliani M M, Deghmane A E, Comanducci M, Brunelli B, Dull P, Pizza M, Taha M K. 2013. Could the multicomponent meningococcal serogroup B vaccine (4CMenB) control *Neisseria meningitidis* capsular group X outbreaks in Africa? Vaccine. 31: 1113-1116.
6. Frasch C E, Preziosi M P, LaForce F M. 2012. Development of a group A meningococcal conjugate vaccine, MenAfriVac™. Hum Vaccin Immunother. 8: 715-724.
7. Boisier P, Nicolas P, Djibo S, Taha M K, Jeanne I, Mainassara H B, Tenebray B, Kairo K K, Giorgini D, Chanteau S. 2007. Meningococcal meningitis: unprecedented incidence of serogroup X-related cases in 2006 in Niger. Clin Infect Dis. 44: 657-663.
8. Taha M K, Parent Du Chatelet I, Schlumberger M, Sanou I, Djibo S, de Chabalier F, Alonso J M. 2002. *Neisseria meningitidis* serogroups W135 and A were equally prevalent among meningitis cases occurring at the end of the 2001 epidemics in Burkina Faso and Niger. J Clin Microbiol. 40: 1083-1084.
9. Collard J M, Issaka B, Zaneidou M, Hugonnet S, Nicolas P, Taha M K, Greenwood B, Jusot J F. 2013. Epidemiological changes in meningococcal meningitis in Niger from 2008 to 2011 and the impact of vaccination. BMC Infect Dis. 13: 576.
10. Terrade A, Collard J M, Nato F, Taha M K. 2013. Laboratory evaluation of a rapid diagnostic test for *Neisseria meningitidis* serogroup A. Trans R Soc Trop Med Hyg.
11. Chanteau S, Sidikou F, Djibo S, Moussa A, Mindadou H, Boisier P. 2006. Scaling up of PCR-based surveillance of bacterial meningitis in the African meningitis belt: indisputable benefits of multiplex PCR assay in Niger. Trans R Soc Trop Med Hyg. 100: 677-680.
12. Chanteau S, Dartevelle S, Mahamane A E, Djibo S, Boisier P, Nato F. 2006. New rapid diagnostic tests for *Neisseria meningitidis* serogroups A, W135, C, and Y. PLoS Med. 3: e337.
13. European Centre for Disease Prevention and Control. 2013. Annual Epidemiological Report 2012. Reporting on 2010 surveillance data and 2011 epidemic intelligence data. Stockholm: ECDC.
14. Micoli F, Romano M R, Tontini M, Cappelletti E, Gavini M, Proietti D, Rondini S, Swennen E, Santini L, Filippini S, Balocchi C, Adamo R, Pluschke G, Norheim G, Pollard A, Saul A, Rappuoli R, MacLennan C A, Berti F, Costantino P. 2013. Development of a glycoconjugate vaccine to prevent meningitis in Africa caused by meningococcal serogroup X. Proc Natl Acad Sci USA. 110: 19077-19082.
15. Kellogg D S, Jr., Peacock W L, Jr., Deacon W E, Brown L, Pirkle D I. 1963. *Neisseria gonorrhoeae*. I. Virulence Genetically Linked to Clonal Variation. J Bacteriol. 85: 1274-1279.
16. Ballard T L, Roe M H, Wheeler R C, Todd J K, Glode M P. 1987. Comparison of three latex agglutination kits and counter immunoelectrophoresis for the detection of bacterial antigens in a pediatric population. Pediatr Infect Dis J. 6: 630-634.
17. Abdillahi H, Poolman J T. 1988. *Neisseria meningitidis* group B serosubtyping using monoclonal antibodies in whole-cell ELISA. Microb Pathog. 4: 27-32.
18. Nato F, Mazie J C, Fournier J M, Slizewicz B, Sagot N, Guibourdenche M, Postic D, Riou J Y. 1991. Production of polyclonal and monoclonal antibodies against group A, B, and C capsular polysaccharides of *Neisseria meningitidis* and preparation of latex reagents. J Clin Microbiol. 29: 1447-1452.
19. Xie O, Bolgiano B, Gao F, Lockyer K, Swann C, Jones C, Delrieu I, Njanpop-Lafourcade B M, Tamekloe T A, Pollard A J, Norheim G. 2012. Characterization of size, structure and purity of serogroup X *Neisseria meningitidis* polysaccharide, and development of an assay for quantification of human antibodies. Vaccine. 30: 5812-5823.
20. Taha M K, Giorgini D. 1995. Phosphorylation and functional analysis of PilA, a protein involved in the transcriptional regulation of the pilin gene in *Neisseria gonorrhoeae*. Mol Microbiol. 15: 667-677.

21. Chanteau S, Rahalison L, Ralafiarisoa L, Foulon J, Ratsitorahina M, Ratsifasoamanana L, Carniel E, Nato F. 2003. Development and testing of a rapid diagnostic test for bubonic and pneumonic plague. Lancet. 361: 211-216.
22. Jaeschke R, Guyatt G H, Sackett D L. 1994. Users' guides to the medical literature. III. How to use an article about a diagnostic test. B. What are the results and will they help me in caring for my patients? The Evidence-Based Medicine Working Group. JAMA. 271: 703-707.
23. Glas A S, Lijmer J G, Prins M H, Bonsel G J, Bossuyt P M. 2003. The diagnostic odds ratio: a single indicator of test performance. J Clin Epidemiol. 56: 1129-1135.
24. Cohen J. 1960. A coefficient of agreement for nominal scales. Edu Psychol Measur. 20: 37-46.
25. Cartwright K A, Reilly S, White D, Stuart J. 1992. Early treatment with parenteral penicillin in meningococcal disease. Bmj. 305: 143-147.
26. Parent du Chatelet I, Traore Y, Gessner B D, Antignac A, Naccro B, Njanpop-Lafourcade B M, Ouedraogo M S, Tiendrebeogo S R, Varon E, Taha M K. 2005. Bacterial meningitis in Burkina Faso: surveillance using field-based polymerase chain reaction testing. Clin Infect Dis. 40: 17-25.
27. Rissin, D M., et al. 2010. Single-molecule enzyme-linked immunosorbent assay detects serum proteins at subfemtomolat concentrations. Nat. Biotechnol. 28: 595-600.
28. Agnememel A. et al. 2015. Development and evaluation of a dipstick diagnostic test for *Neisseria meningitidis* serogroup X. J Clin Microbiol 53: 449-454.

The invention claimed is:

1. Purified polyclonal antibodies specific for the capsular polysaccharides of *Neisseria meningitidis* serogorup X bacteria (NmX), wherein said antibodies are obtained by immunization of a mammal with whole inactivated *Neisseria meningitidis* serogroup X followed by purification of said antibodies from serum of the immunized mammal by first affinity chromatography with protein G followed by second affinity purification with purified *Neisseria meningitidis* serogorup X capsular polysaccharides (cpsX), wherein said purified antibodies detect *Neisseria meningitidis* serogroup X bacteria (NmX) in a biological fluid sample in an immunoassay performed without culturing said biological fluid and wherein said antibodies do not cross-react with *Neisseria meningitidis* bacteria of serogroups A, B, C, Y and W.

2. A diagnostic agent comprising the polyclonal antibodies of claim 1 linked directly or indirectly, covalently or noncovalently to a detection label.

3. A diagnostic kit for detecting *Neisseria meningitidis* serogroup X bacteria comprising the polyclonal antibodies of claim 1 and means for detecting the production of an immune complex between said antibodies and the NmX capsular polysaccharides (cpsX).

4. The diagnostic kit of claim 3, for detecting the NmX in a biological fluid sample without culturing said biological fluid sample.

5. The diagnostic kit of claim 4, wherein the kit allows the detection of the NmX by the immunoassay.

6. The diagnostic kit of claim 5, wherein the immunoassay has a sensitivity of at least 90%.

7. A dipstick diagnostic test for NmX comprising a membrane, wherein said membrane comprises:

(a) a first zone comprising the polyclonal antibodies of claim 1 conjugated to a detection label;

(b) a control zone comprising an immobilized control polypeptide that recognizes the polyclonal antibodies according to claim 1 and (c) a capture zone comprising the polyclonal antibodies according to claim 1 immobilized thereon as capture antibodies.

8. A dipstick diagnostic test for NmX comprising a membrane, wherein said membrane comprises:

(a) a first zone comprising the polyclonal antibodies of claim 1 conjugated to a detection label;

(b) a control zone comprising immobilized control antibodies that recognize the polyclonal antibodies according to claim 1 and (c) a capture zone comprising the polyclonal antibodies according to claim 1 immobilized thereon as capture antibodies.

9. The dipstick diagnostic test of claim 8, wherein the polyclonal antibodies are rabbit antibodies and the immobilized control antibodies are anti-rabbit antibodies.

10. The diagnostic kit of claim 4, wherein the biological fluid sample is chosen from cerebrospinal fluid, blood, serum, and urine.

11. The diagnostic kit of claim 5, wherein said immunoassay is a rapid diagnostic test.

* * * * *